United States Patent [19]

Wade et al.

[11] 4,148,798
[45] Apr. 10, 1979

[54] [(1,1-DIOXO-1,2-BENZISOTHIAZOL-3-YL)AMINO]ALKANOIC ACIDS AND ESTERS THEREOF

[75] Inventors: Peter C. Wade, Pennington, N.J.; B. Richard Vogt, Yardley, Pa.

[73] Assignee: E. R. Squibb & Sons, Inc., Princeton, N.J.

[21] Appl. No.: 875,022

[22] Filed: Feb. 3, 1978

[51] Int. Cl.² .......................................... C07D 275/06
[52] U.S. Cl. ...................................... 260/301; 424/270
[58] Field of Search ........................... 260/304 A, 301

[56] References Cited
U.S. PATENT DOCUMENTS

| | | | |
|---|---|---|---|
| 2,751,392 | 6/1956 | Grogan et al. | 260/301 |
| 3,225,056 | 12/1965 | Traverso et al. | 260/301 |
| 3,271,406 | 9/1966 | Traverso et al. | 260/301 |
| 3,457,272 | 7/1969 | Crook et al. | 260/301 |

OTHER PUBLICATIONS

J. Med. Chem. 10(5), 840–844, 844–849, 849–852, (1967).

Primary Examiner—Paul M. Coughlan, Jr.
Assistant Examiner—Lisa Jones
Attorney, Agent, or Firm—Lawrence S. Levinson; Merle J. Smith

[57] ABSTRACT

[(1,1-Dioxo-1,2-benzisothiazol-3-yl)amino]alkanoic acids, esters and salts thereof which have the general formula

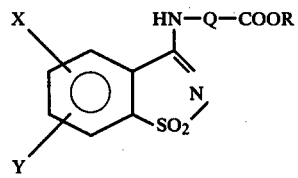

are useful as anti-inflammatory agents.

9 Claims, No Drawings

[(1,1-DIOXO-1,2-BENZISOTHIAZOL-3-YL)AMINO]ALKANOIC ACIDS AND ESTERS THEREOF

SUMMARY OF THE INVENTION

This invention relates to new [(1,1-dioxo-1,2-benzisothiazol-3-yl)amino]alkanoic acids, esters and salts thereof which have the general formula

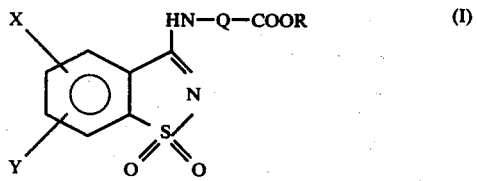

wherein
R is hydrogen or lower alkyl;
Q is lower alkylene of up to 7 carbons or cyclo-lower alkyl of 3 to 7 carbons;
X is hydrogen, halogen, lower alkyl, lower alkoxy or nitro.
Y is hydrogen, lower alkoxy or halogen.

DETAILED DESCRIPTION

The lower alkyl groups represented by the symbols are straight or branched chain aliphatic hydrocarbon radicals having up to 7 carbon atons, for example, methyl, ethyl, propyl, isopropyl, butyl, isobutyl, t-butyl and the like. The lower alkylene radicals are straight and branched chain radicals of the same type. The $C_1$-$C_4$ and especially the $C_1$-$C_3$ groups are preferred.

The lower alkoxy groups are also similar groups having up to 7 carbons like methoxy, ethoxy, propoxy, isopropoxy, butoxy, isobutoxy, t-butoxy, etc. The $C_1$-$C_4$ and especially $C_1$-$C_3$ groups are similarly preferred.

The cycloalkyl groups are the 3 to 7 carbon alicyclics cyclopropyl, cyclobutyl, cyclohexyl and cycloheptyl, the cyclopentyl and cyclohexyl (especially cyclohexyl) groups being preferred.

The halogens are the four common halogens, chlorine and bromine being preferred in that order.

When Y is other than hydrogen, X represents the same substituent as Y.

The preferred compounds of formula I are those wherein X and Y are both hydrogen, R is hydrogen or lower alkyl, especially ethyl, and Q is lower alkylene, especially having 1 to 4 carbons.

The products of formula I are produced by reacting a 3-halo-1,2-benzisothiazole, 1,1-dioxide having the formula

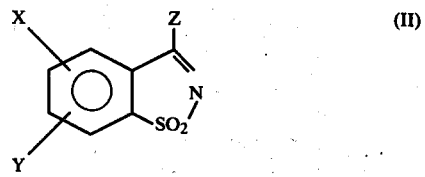

wherein Z is halogen, preferably chlorine or bromine, especially chlorine, with an aminoalkanoic acid ester having the formula $$H_2N-Q-COOR \qquad (III)$$

wherein R is lower alkyl in an inert organic solvent like dioxane, benzene, dimethylformamide, dimethoxyethane, or the like in the optional presence of a basic acid acceptor, e.g., potassium carbonate, sodium carbonate, a trialkylamine like triethylamine or pyridine, or the like, preferably at an elevated temperature, e.g., at reflux temperature.

The resulting ester can then be converted to the free acid (R═H) by a conventional technique such as hydrolysis with dilute hydrochloric acid.

The products of formula I form salts with bases, e.g., alkali metal salts like sodium and potassium salts, alkaline earth metal salts like calcium and magnesium salts, alkylamine salts like methylamine, ethylamine, dimethylamine, triethylamine salts, etc.

The starting materials of formula II are produced from saccharin or substituted saccharins which have the formula

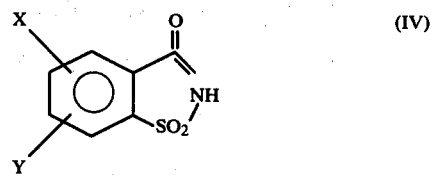

by reaction with thionyl chloride in an inert organic solvent like dioxane in the presence of dimethylformamide catalyst.

The new compounds of this invention have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally or parenterally in dosages of about 5 to 150 mg/kg/day, preferably 10 to 75 mg/kg/day, in single or 2 to 4 divided doses, as indicated by the Mouse Active Arthus or Delayed Hypersensitivity Reaction assays. The active substance can be utilized in compositions such as tablets, capsules, solutions or suspensions containing up to about 500 mg. per unit of a compound or mixture of compounds of formula I. They can be compounded in conventional manner with a physiologically acceptable vehicle or carrier, excipient, binder, preservative, stabilizer, flavor, etc., as called for by accepted pharmaceutical practice.

The following examples are illustrative of the invention and constitute especially preferred embodiments. They also serve as models for the preparation of other members of the group which can be made by suitable substitution of the starting materials. All temperatures are in degrees Celsius.

EXAMPLE 1

4-[(1,1-Dioxo-1,2-benzisothiazol-3-yl)amino]butanoic acid, ethyl ester (a) 100 g. (545 mM) of benzisothiazole 1,1-dioxide, 100 ml. thionyl chloride, 4 ml. of dimethylformamide, and 400 ml. of dioxane are refluxed overnight. Thionyl chloride (50 ml.) and dimethylformamide (1 ml.) are added to the reaction mixture which is again refluxed overnight. The reaction mixture is evaporated to dryness and the residue recrystallized from toluene to obtain 73.4 g. of 3-chloro-1,2-benzisothiazole-1,1-dioxide, m.p. 140°–145°.

(b) 4.07 ml (29.2 mM) of triethylamine is added to 5.0 g. (29.2 mM) of ethyl 4-aminobutyrate hydrochloride, suspended in 75 ml of dioxane. After stirring for 5 minutes, 5.88 g. (29.2 mM) of 3-chloro-1,2-benzisothiazole 1,1-dioxide is added and the mixture is refluxed for one hour. The solvent is evaporated in vacuo and the residue is taken up in chloroform, washed with water, and evaporated to dryness. The residual 4-[(1,1-dioxo-1,2-benzisothiazol-3-yl)amino]-butanoic acid, ethyl ester is recrystallized from 40 ml. of methanol/water, yield 3.72 g., m.p. 125°-127°.

EXAMPLE 2

2-[(1,1-Dioxo-1,2-benzisothiazol-3-yl)amino]acetic acid, ethyl ester 15.0 g. (74.4 mM) of 3-chloro-1,2-benzisothiazole 1,1-dioxide (prepared as in Example 1), 10.4 g. (74.4 mM) of glycine ethyl ester, hydrochloride and 20.4 ml. (148.8 mM) of triethylamine are refluxed in 250 ml of dioxane for 2 hours. The dioxane is evaporated and the residue is taken up in chloroform which is washed with water (2 x) and evaporated. The residue 2-[(1,1-dioxo-1,2-benzisothiazol-3-yl)amino]acetic acid, ethyl ester is recrystallized once from 150 ml of methanol/water (1:1) and once from 200 ml. of water to give 2-[(1,1-dioxo-1,2-benzisothiazol-3-yl)amino]acetic acid, ethyl ester as yellow needles, yield 14.35 g., m.p. 166°-167°.

EXAMPLE 3

2-[(1,1-Dioxo-1,2-benzisothiazol-3-yl)amino]acetic acid 8.8 g. (32.8 mM) of 2-[(1,1-dioxo-1,2-benzisothiazol-3-yl)amino]acetic acid, ethyl ester (prepared as in Example 2) is refluxed in 100 ml of 1% hydrochloric acid for 3 hours. After standing overnight at room temperature, the product crystallizes as white plates and is filtered out, washed with water and recrystallized from 150 ml water to yield 6.4 g. of 2-[(1,1-dioxo-1,2-benzisothiazol-3-yl)amino]acetic acid, m.p. 259°-260°. 3 g. of this product is added to an aqueous sodium hydroxide solution containing one equivalent of base and warmed to obtain a homogeneous solution. The sodium salt is obtained by lyophilization of the resulting solution.

EXAMPLE 4

4-[(1,1-Dioxo-1,2-benzisothiazol-3-yl)amino]butanoic acid 5.68 g. (28.1 mM) of 3-chloro-1,2-benzisothiazole, 1,1-dioxide (prepared as in Example 1), 4.8 g. (28.1 mM) of ethyl-4-aminobutyrate hydrochloride and 7.84 ml. (56.2 mM) of triethylamine are refluxed in 100 ml. of dioxane for one hour. The solvent is evaporated and the residue refluxed in 1% hydrochloric acid for 2.5 hours. The product crystallizes out overnight at room temperature. The product, 4-[(1,1-dioxo-1,2-benzisothiazol-3-yl)amino]butanoic acid is filtered out, washed with water, and recrystallized from 150 ml. water, yield 4.2 g., m.p. 200°-202°.

EXAMPLE 5

4-[(5-Chloro-1,1-dioxo-1,2-benzisothiazole-3-yl)amino]-cyclohexanecarboxylic acid ethyl ester By substituting 4-aminocyclohexane carboxylic acid ethyl ester for the ethyl-4-aminobutyrate hydrochloride in the procedure of Example 1, and 3,5-dichloro-1,2-benzisothiazole, 1,1-dioxide for the 3-chloro-1,2-benzisothiazole, 1,1-dioxide, 4-[(5-chloro-1,1-dioxo-1,2-benzisothiazol-3-yl)amino]cyclohexanecarboxylic acid, ethyl ester is obtained.

The following additional esters are produced by the procedure of Example 1 by replacing the 3-chloro-1,2-benzisothiazole, 1,1-dioxide, with its X and/or Y substituted analog and/or replacing the ethyl 4-aminobutyrate with the analogous aminoalkanoic acid lower alkyl ester. The acids are obtained by hydrolyzing the ester as in Example 3.

| Example | X | Y | Q | R |
|---|---|---|---|---|
| 6 | 6-Cl | H | —(CH$_2$)$_4$— | —C$_3$H$_7$ |
| 7 | 6-Br | H | —(CH$_2$)$_3$— | —C$_4$H$_9$ |
| 8 | 6-Br | H | —(CH$_2$)$_3$— | H |
| 9 | 6-Cl | 7-Cl | —(CH$_2$)$_3$— | —C$_2$H$_5$ |
| 10 | 8-Cl | 5-Cl | —(CH$_2$)$_2$— | —C$_2$H$_5$ |
| 11 | H | H | —(CH$_2$)$_6$— | —C$_7$H$_{15}$ |
| 12 | 6-CH$_3$ | H | —(CH$_2$)$_2$— | H |
| 13 | 6-OCH$_3$ | 7-OCH$_3$ | —CH$_2$— | —C$_2$H$_5$ |
| 14 | 6-OCH$_3$ | 7-OCH$_3$ | —CH$_2$— | H |
| 15 | 6-NO$_2$ | H | —(CH$_2$)$_2$— | —C$_2$H$_5$ |
| 16 | H | H | cyclopentyl | —C$_2$H$_5$ |
| 17 | 6-Cl | H | cyclohexyl | —C$_2$H$_5$ |
| 18 | H | H | cyclohexyl | H |
| 19 | 6-OC$_2$H$_5$ | 7-OC$_2$H$_5$ | —(CH$_2$)$_5$— | —C$_2$H$_5$ |
| 20 | 7-OCH$_3$ | 8-OCH$_3$ | —(CH$_2$)$_2$— | —C$_2$H$_5$ |
| 21 | 5-F | H | —(CH$_2$)$_3$— | —CH$_3$ |

What is claimed is:

1. A compound of the formula wherein
R is hydrogen or lower alkyl;
Q is lower alkylene, cyclopentyl or cyclohexyl;
X is hydrogen, halogen, lower alkyl, lower alkoxy or nitro;
Y is hydrogen, lower alkoxy or halogen, X being the same as Y when Y is other than hydrogen; and basic salts thereof.

2. A compound as in claim 1 wherein X and Y are both hydrogen.

3. A compound as in claim 1 wherein X and Y are both hydrogen; R is hydrogen or lower alkyl; and Q is lower alkylene.

4. A compound as in claim 3 wherein R is ethyl.

5. A compound as in claim 2 wherein R is ethyl and Q is (CH$_2$)$_3$.

6. A compound as in claim 2 wherein R is ethyl and Q is CH$_2$.

7. A compound as in claim 2 wherein R is hydrogen and Q is CH$_2$.

8. A compound as in claim 2 wherein R is hydrogen and Q is (CH$_2$)$_3$.

9. A compound as in claim 1 wherein Y is hydrogen.

* * * * *